US012797583B2

(12) United States Patent
Hwang et al.

(10) Patent No.: US 12,797,583 B2
(45) Date of Patent: Nov. 17, 2026

(54) INPUT MECHANISM FOR PREVENTION OF UNINTENDED MOTION

(71) Applicant: Canon U.S.A., Inc., Melville, NY (US)

(72) Inventors: Charles George Hwang, Wellesley, MA (US); Takahisa Kato, Brookline, MA (US)

(73) Assignee: Canon U.S.A., Inc., Melville, NY (US)

(*) Notice: Subject to any disclaimer, the term of this patent is extended or adjusted under 35 U.S.C. 154(b) by 1266 days.

(21) Appl. No.: 17/545,798

(22) Filed: Dec. 8, 2021

(65) Prior Publication Data

US 2022/0203071 A1 Jun. 30, 2022

Related U.S. Application Data

(60) Provisional application No. 63/132,120, filed on Dec. 30, 2020.

(51) Int. Cl.
*A61M 25/01* (2006.01)
*A61M 25/00* (2006.01)

(52) U.S. Cl.
CPC .... *A61M 25/0158* (2013.01); *A61M 25/0133* (2013.01); *A61M 2025/0001* (2013.01); *A61M 2205/3306* (2013.01); *A61M 2205/3327* (2013.01); *A61M 2205/502* (2013.01)

(58) Field of Classification Search
CPC .......... A61M 25/0158; A61M 25/0133; A61M 2025/0001; A61M 2205/3306; A61M 2205/3327; A61M 2205/502; A61M 2205/276; A61M 2205/3331; A61M 2230/63; A61M 2230/65
See application file for complete search history.

(56) References Cited

U.S. PATENT DOCUMENTS

| | | | | |
|---|---|---|---|---|
| 5,389,100 | A | 2/1995 | Bacich et al. | |
| 5,434,457 | A | 7/1995 | Josephs et al. | |
| 8,816,962 | B2 | 8/2014 | Obermeyer et al. | |
| 9,161,817 | B2 | 10/2015 | Olson et al. | |
| 9,888,973 | B2 | 2/2018 | Olson et al. | |
| 10,512,515 | B2 | 12/2019 | Bailey | |
| 2009/0221914 | A1* | 9/2009 | Barrett | A61M 5/14216 600/431 |
| 2010/0256558 | A1* | 10/2010 | Olson | A61B 34/77 604/95.01 |
| 2019/0380802 | A1* | 12/2019 | Savall | A61B 34/74 |
| 2020/0155252 | A1 | 5/2020 | Diolaiti et al. | |
| 2022/0382364 | A1* | 12/2022 | Verner | G06F 3/011 |

FOREIGN PATENT DOCUMENTS

| | | | |
|---|---|---|---|
| JP | 2004326713 | A | 11/2004 |
| JP | 2020529237 | A | 10/2020 |
| WO | 2019/027922 | A1 | 2/2019 |

* cited by examiner

*Primary Examiner* — Tasnim Mehjabin Ahmed
(74) *Attorney, Agent, or Firm* — Canon U.S.A., Inc. IP Division

(57) ABSTRACT

A medical apparatus includes a medical device capable of maneuvering within a patient, an input device configured to be operated by a hand of a user, one or more sensors for sensing whether the hand of the user is interacting with the input device, and a controller configured to determine whether the one or more sensors is sensing that the hand of the user is interacting with the input device, and in a case that the controller determines that the one or more sensors is sensing that the hand of the user is not interacting with the input device, prevent actuation of the medical device.

17 Claims, 11 Drawing Sheets

*Intuitive Ion System*

*Intuitive Ion System*

*Safety Foot Pedal*

*Figs. 1 and 3 of Japanese Publication No. 2004326713*

INPUT MECHANISM FOR PREVENTION OF UNINTENDED MOTION

CROSS REFERENCE TO RELATED APPLICATIONS

The present application claims the benefit of priority from U.S. Provisional Application No. 63/132,120 filed Dec. 30, 2020, which is hereby incorporated by reference herein in its entirety.

BACKGROUND

Field of the Disclosure

The present disclosure generally relates to medical equipment and, more particularly to an apparatus, method, and storage medium to prevent unintended motion.

Description of the Related Art

Medical equipment, such as a robotic catheter system or other types of equipment, is subject to inadvertent or unintended motion. An Intuitive Ion System, for example, is a robotic-assisted platform for minimally invasive biopsies of peripheral lung lesions and is manufactured by Intuitive Surgical, Inc. The Intuitive Ion System is shown in FIG. 8 and a console of the system is shown in FIG. 9. The system has a robotic catheter controlled by the console that has several directional controls (see U.S. Pat. No. 10,512,515 to Bailey). In order to lessen the possibility of inadvertent catheter movement, such as if a control cart tips over, there are sensors which detect a user's wrist. Catheter movement commands are ignored unless the user's wrist is detected on a wrist rest.

A common safety device is a safety foot pedal, as shown in FIG. 10. Until a user depresses the foot pedal, the operation of the equipment is disabled.

Japanese Publication No. 2004326713 discloses a force sensing joystick, shown in FIG. 11, with contact sensors at the operation end of the joystick. The force sensing joystick illustrates how different functions are enabled depending on the finger position, e.g., in one finger position, the joystick causes a cursor to move. In another, it causes a page to scroll.

Surgical robots, by their very nature, navigate to medically sensitive parts of the body, with little margin for error. Critical to the safety of the patients is to prevent inadvertent movement of the robotic catheter. Such as if the control cart is knocked over or the handle held controller is dropped.

However, also critical is the ease of use and speed which a user can command catheter movement. If the locking mechanism has to minimally, alter the normal workflow of device use, the efficiency of the user becomes limited.

The Intuitive Ion System has a standalone floor-mounted controller with wrist detection to minimize the risk of unintended motion command. However, the physician's wrist is forced to be in this position. This limits efficiency for the physician to perform other tasks like biopsy tool handling while the physician is using the controller.

A need exists to overcome the drawbacks identified above.

SUMMARY

The present disclosure advantageously provides an apparatus, method, and storage medium to prevent unintended motion while providing better work efficiency to users.

According to an aspect of the present disclosure, a medical apparatus includes a medical device capable of maneuvering within a patient, an input device configured to be operated by a hand of a user, one or more sensors for sensing whether the hand of the user is interacting with the input device, and a controller configured to determine whether the one or more sensors is sensing that the hand of the user is interacting with the input device, and in a case that the controller determines that the one or more sensors is sensing that the hand of the user is not interacting with the input device, prevent actuation of the medical device.

Further features of the present disclosure will become apparent from the following description of exemplary embodiments with reference to the attached drawings, where like structure is indicated with like reference numerals.

DESCRIPTION OF THE EMBODIMENTS

Various exemplary embodiments, features, and aspects of the disclosure that relate to an apparatus, method, or storage medium to prevent unintended motion will be described below with reference to the drawings that may have different characteristics, advantages, disadvantages, performance parameters, or the like.

In the present disclosure, medical apparatus, equipment, device or instrument configurations to prevent unintended motion are described that functionally implement intravascular imaging modalities including, for example, CT (computed tomography), MRI (magnetic resonance imaging), IVUS (intravascular ultrasound), positron emission tomography (PET), X-ray imaging, angiography, optical coherence tomography (OCT), multi-modality OCT (MMOCT), near infrared auto fluorescence (NIRAF), spectrally encoded endoscopy (SEE), combinations or hybrids thereof, or the like. The present disclosure is not limited to any particular configuration.

Figure 1:
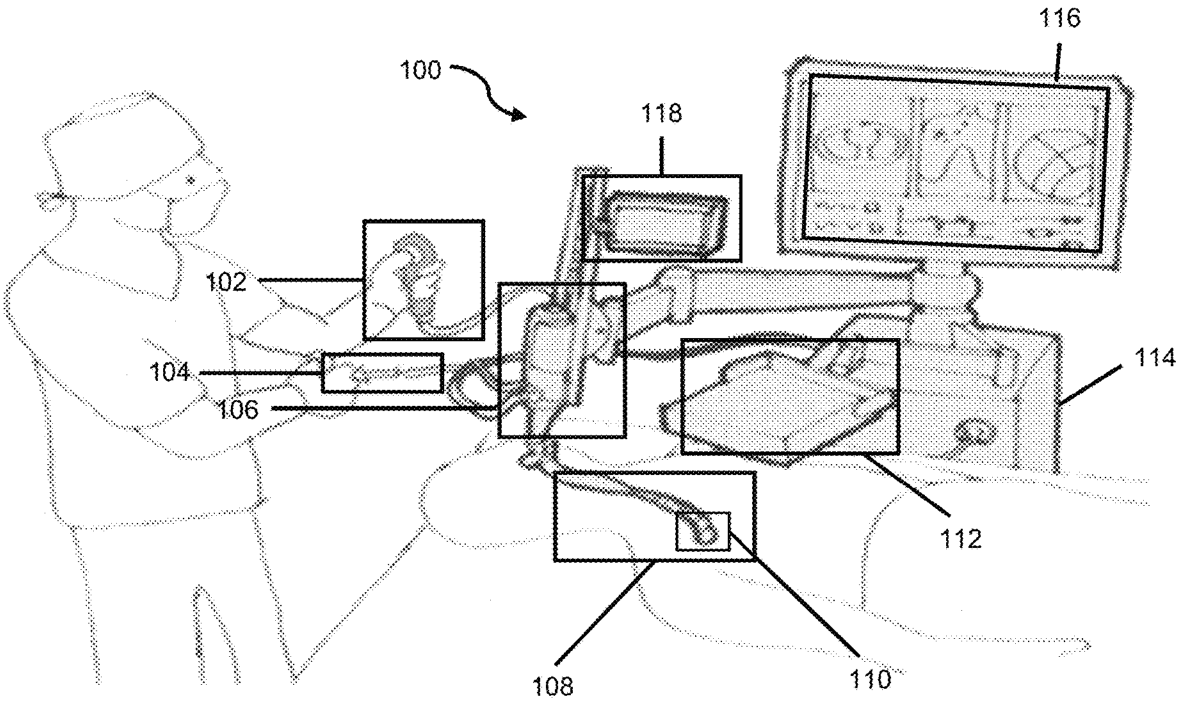
FIG. 1 illustrates an exemplary apparatus to prevent unintended motion according to some embodiments.
Figure 2:
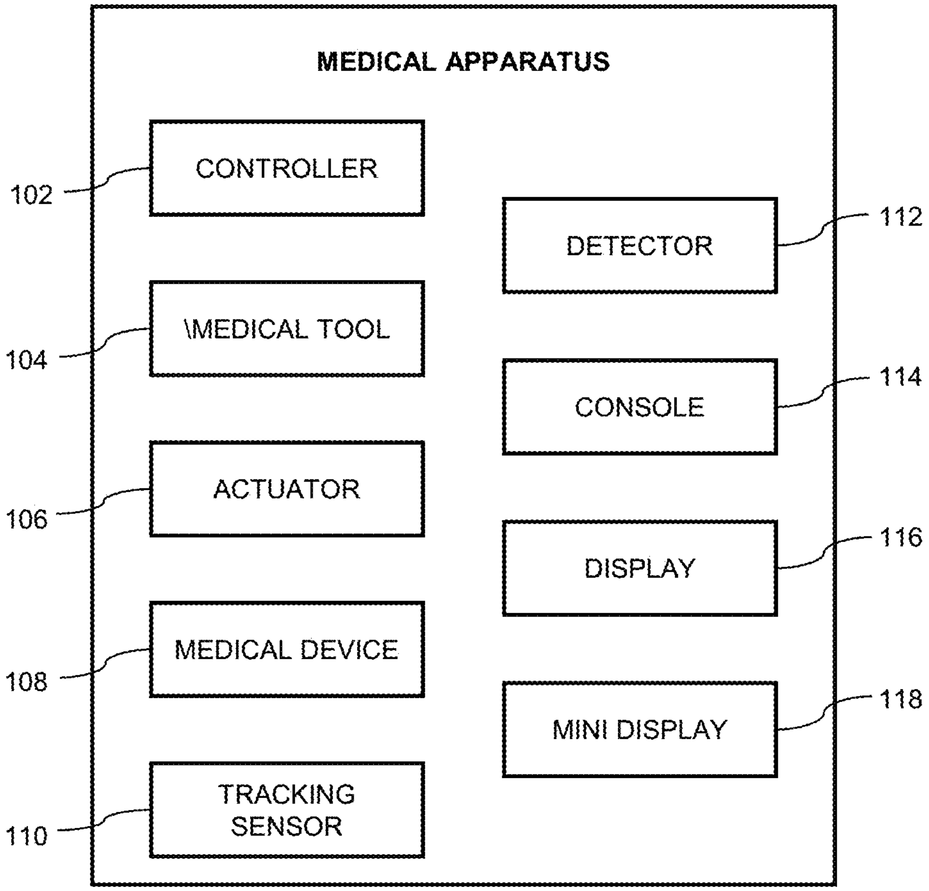
FIG. 2 is a block diagram of the apparatus of FIG. 1.

FIG. 1 illustrates a robotic catheter assembly or snake configuration as an exemplary medical apparatus 100 according to some embodiments. FIG. 2 shows a hardware configuration of the robotic catheter 100.

The robotic catheter 100 includes one or more of a hand-held controller 102, a medical tool 104, an actuator 106, a medical device 108, a tracking sensor 110, a detector 112, a console 114, a display 116, and a mini display 118, and can include other elements or components. Throughout the present disclosure, the medical tool 104 is referred to as a "biopsy tool" and the medical device 108 is referred to as a "catheter", but these are exemplary and one or more of a variety of other types of tools, devices, configurations, or arrangements also falls within the scope of the present disclosure including, for example, snake robotic catheter, a sheath, guidewire, needle, probe, forceps, or the like.

The robotic catheter 100 according to some embodiments can implement functioning through use of one or more processes, techniques, algorithms, or the like, that can prevent unintended motion while providing better work efficiency to physicians during a medical procedure.

The controller 102 has a housing with an elongated handle or handle section which can be manually grasped, and one or more input devices including, for example, a lever or a button or another input device that allows a user, such as a physician, to send a command to the medical apparatus 100 to move the catheter 108. The controller 102 executes software, computer instructions, algorithms, or the like, so a user can complete all operations with the hand-held controller 102 by holding it with one hand.

The controller 102 can include a sensor in the form of a movement-unlocking sensor to distinguish an intended operation by a user from unintended operations to ensure catheter movement only occurs when the controller 102 is held and operated by the user intentionally. The sensor can be an optical, electrical, mechanical, or other type of sensor so the catheter only moves when the sensor detect a finger or thumb on the joystick, or a finger or thumb on the housing. This prevents movement if the controller 102 is dropped.

The medical tool 104 can be a biopsy tool or other type of tool. The actuator 106 can include one or more motors and drives each section of the catheter 108. The controller 102, medical device 108, console 114, and other elements are interconnected to the actuator 106. The controller 102 includes at least one processor and is configured to control the medical device 108 through the actuator 106, and to control the actuator 106 in accordance with the manipulation by a user.

The medical device 108 can be configured as a catheter or another type of medical device. The tracking sensor no can be an electromagnetic tracking sensor (EM tracking sensor) and is attached to the tip of the catheter 108. The detector 112 detects a position of the EM tracking sensor no and outputs the detected positional information to the controller 102 and/or the console 114. The controller 102 receives the positional information of the catheter tip directly from the tracking sensor no or from the detector 112.

The console 114 executes software, computer instructions, algorithms, or the like, and controls to display a navigation screen on the display 116 and other types of imagery or information on the mini-display 118. The console 114 can generate a three-dimensional (3D) model of an internal branching structure, for example, lungs or other internal structures, of a patient based on medical images such as CT, MRI, or the like. Alternatively, the 3D model may be received by the console 114 from another device.

The console 114 acquires catheter position information from the detector 112. Alternatively, the console 114 can acquire the catheter position information directly from the tracking sensor no.

The console 114 generates and outputs the navigation screen to the display 104 based on the 3D model and the catheter positional information by executing the software. The navigation screen can indicate a current position of the catheter 110 on the 3D model. By the navigation screen, a user can recognize the current position of the catheter 110 in the branching structure.

The console 114 can execute a correction of the acquired 3D model based on the catheter positional information so as to minimize a divergence between the catheter position and a path mapped out on the 3D model.

The display 116 and/or the mini display 118 can be a display device configured, for example, as a monitor, an LCD (liquid-crystal display), an LED (light-emitting diode) display, an OLED (organic LED) display, a plasma display, an organic electro luminescence panel, or the like. Based on the control of the apparatus, the navigation screen may be displayed on the display 116 showing one or more images being captured, captured images, captured moving images recorded on the storage unit, or the like. The mini display 118 is smaller than the display 116 and can they can each display similar or other types of imagery and/or information.

Figure 3:
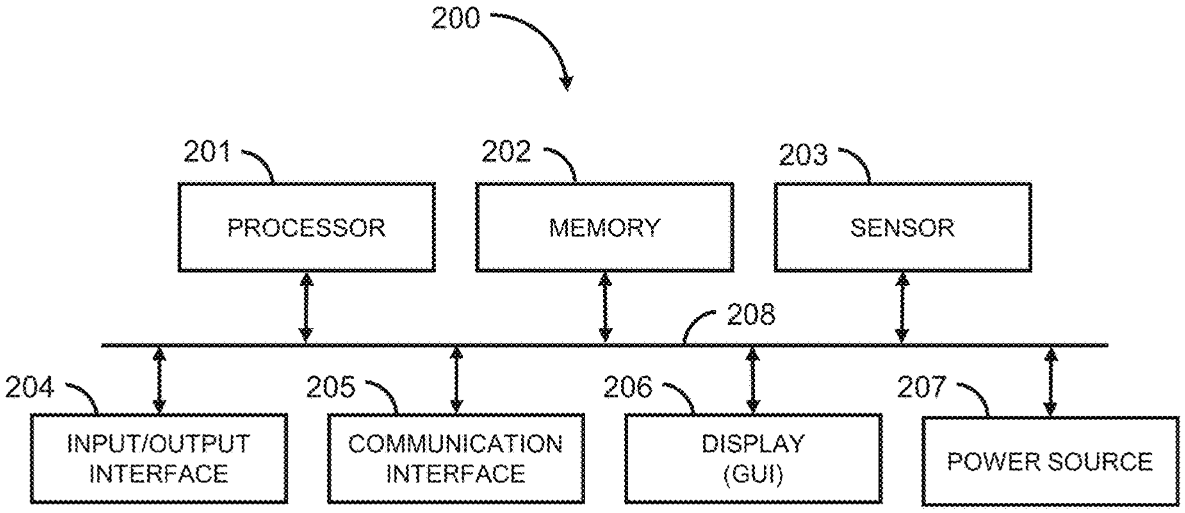
FIG. 3 is a block diagram of the controller of FIG. 2.

The controller 102 and/or the console 114 can include one or more or a combination of levers, keys, buttons, switches, a mouse, a keyboard, or the like, to control the elements of the apparatus 100 and each has configurational components 200, as shown in FIG. 3, that include one or more or a combination of a processor 201, a memory 202, a sensor 203, an input and output (I/O) interface 204, a communication interface 205, a display 206, a power source 207, and can include other elements or components. The apparatus 100 can be interconnected with medical instruments or a variety of other devices, and can be controlled independently, externally, or remotely by the controller 102 and/or the console 114.

The processor 201 can be configured as a control circuit or circuitry for performing overall control of the medical apparatus 100, and can execute a program, instructions, code or software stored in the memory 202 to perform various data processing, computation, algorithmic tasks, or other functions of the medical apparatus 100. The memory 202 can store the program, software, computer instructions, information, other data, or combinations thereof. The memory 202 is used as a work memory. The processor 201, which may include one or more processors, circuitry, or a combination thereof, executes the software developed in the memory 202.

The sensor 203 can monitor, measure or detect various types of data of the medical apparatus 100, and can transmit or send the sensor readings or data to a host through a network. The I/O interface 204 can interconnect various components with the medical apparatus 100 to transfer data or information to or from the medical apparatus 100. The I/O interface 204 can input the catheter positional information to the console 114 and can output information for displaying a navigation screen to the display 116. The communication interface 205 can interconnect various components with the medical apparatus 100 to facilitate communication to or from or the medical apparatus 100.

The display 206 corresponds to the display 116 and/or the display 118 and can present a display to a user to view images, data or other information, and can be configured as an LCD or other type of display. The controller 102 and/or the console 114 can perform display control of the display 206 and control of input of various kinds of setting or default information set by the input/output interface 204 and the communication interface 205, and to provide inputs to the medical apparatus 100.

The power source 207 provides power to the medical apparatus boo to maintain a regulated power supply to the medical apparatus 100, and can operate in a power-on mode, a power-off mode, and can operate in other modes. The power source 107 can include a battery contained in the medical apparatus boo and can include an external power source such as line power or AC power from a power outlet that can interconnect with the medical apparatus 100 through an AC/DC adapter and a DC/DC converter, or an AC/DC converter in order to adapt the power voltage from a source into one or more voltages used by components in the medical apparatus 100.

The components are connected together by a bus 208 so that the components can communicate with each other. The bus 208 connects the medical apparatus 100 to input devices, output devices, communication devices, or other devices. The input devices are configured to enable the user to communicate information and select commands to the medical apparatus 100, and can include one or more or a combination of a mouse, keyboard, touchscreen, or the like, with keys or buttons with alphanumeric, icon, emoji, or other types of symbols. The output devices are configured to display data or images generated by the medical apparatus 100, and can include printers, display devices, or other output configurations.

The bus 208 transmits and receives data between these pieces of hardware connected together, or transmits a command from the processor 201 to the other pieces of hardware. The components can be implemented by one or more physical devices that may be coupled to the processor 201 through a communication channel. For example, the controller 102 and/or the console 114 can be implemented using circuitry in the form of ASIC (application specific integrated circuits) or the like. Alternatively, the controller 102 and/or the console 114 can be implemented as a combination of hardware and software, where the software is loaded into a processor from a memory or over a network connection. Functionality of the controller 102 and/or the console 114 can be stored on a storage medium, which may include RAM (random-access memory), ROM (read only memory), magnetic or optical drive, diskette, cloud storage, or the like.

The sensor 203 can be in the form of a movement-unlocking sensor to distinguish an intended operation by a user from unintended operations to ensure catheter movement only occurs when the controller 102 is held and operated by the user intentionally. The sensor 203 can include one or more or a combination of a processor, detection circuitry, memory, hardware, software, firmware, and can include other circuitry, elements, or components. The sensor 203 can be a plurality of sensors and acquires sensor information output from one or more sensors that detect motion, current position and movement of components interconnected with the medical apparatus 100. The sensor 103 can include a multi-axis acceleration or accelerometer sensor and a multi-axis gyroscope sensor, can be a combination of an acceleration and gyroscope sensors, can include other sensors, and can be configured through the use of a piezoelectric transducer, a mechanical switch, a single axis accelerometer, a multi-axis accelerometer, or other types of configurations. The sensor 103 can monitor, detect, measure, record, or store physical, operational, quantifiable data or other characteristic parameters of the medical apparatus 100 including one or more or a combination of an impact, shock, drop, fall, movement, acceleration, deceleration, velocity, rotation, temperature, pressure position, orientation, motion, or other types of data of the medical apparatus 100 in multiple axes, in a multi-dimensional manner, along an x axis, y axis, z axis, or any combination thereof, and can generate sensor readings, information, data, a digital signal, an electronic signal, or other types of information corresponding to the detected state. The medical apparatus 100 can transmit or send the sensor reading data wirelessly or in a wired manner to a remote host or server. The sensor 203 can be interrogated and can generate a sensor reading signal or information that can be processed in real time, stored, post processed at a later time, or combinations thereof. The information or data that is generated by the sensor 203 can be processed, demodulated, filtered, or conditioned to remove noise or other types of signals. The sensor 203 can include one or more or a combination of an acceleration, deceleration, or accelerometer sensor, a gyroscope sensor, a power sensor, a battery sensor, a proximity sensor, a motion sensor, a position sensor, a rotation sensor, a magnetic sensor, a barometric sensor, an illumination sensor, a pressure sensor, an angular position sensor, a temperature sensor, an altimeter sensor, an infrared sensor, a sound sensor, an air monitoring sensor, a piezoelectric sensor, a strain gauge sensor, a sound sensor, a vibration sensor, a depth sensor, and can include other types of sensors.

The acceleration sensor, for example, can sense or measure the displacement of mass of a component of the medical apparatus 100 with a position or sense the speed of a motion of the component of the medical apparatus 100. The gyroscope sensor can sense or measure angular velocity or an angle of motion and can measure movement of the medical apparatus 100 in up to six total degrees of freedom in three-dimensional space including three degrees of translation freedom along cartesian x, y, and z coordinates and orientation changes between those axes through rotation along one or more or of a yaw axis, a pitch axis, a roll axis, and a horizontal axis. Yaw is when the component of the medical apparatus 100 twists left or right on a vertical axis. Rotation on the front-to-back axis is called roll. Rotation from side to side is called pitch. The sensor 203 can monitor shock or drop impact with low power consumption, dynamic range, and bandwidth to accurately detect and capture shock events and convert the sensor readings to a digital signal for additional or post processing. An entire shock profile can be characterized by its peak amplitude and pulse width for further analysis. The processor 201 of the component of the medical apparatus 100 can also interrogate the capacity of the power source, and can warn a user to replace the battery at a time when a value of the battery capacity falls below a predetermined threshold amount.

The acceleration sensor can include, for example, a gravity sensor, a drop detection sensor, or the like. The gyroscope sensor can include an angular velocity sensor, a hand-shake correction sensor, a geomagnetism sensor, or the like. The position sensor can be a global positioning system (GPS) sensor that receives data output from a GPS. The longitudinal and latitude of a current position can be obtained from access points of a radio frequency identification device (RFID) and a WiFi device and information output from wireless base stations, for example, so that these detections may be used as position sensors. These sensors can be arranged internally or externally of the medical apparatus 100.

When the component of the medical apparatus 100 moves, an acceleration change, deceleration change, or rotation around the gravity axis can be detected and the sensor 203 can output the information about the detected change or rotation. The component of the medical apparatus 100 can acquire information about the change or rotation output from the sensor 103 as sensor information. In response to movement of the component of the medical apparatus 100, the sensor 203 can obtain positional information (longitude and latitude, for example) indicative of a place at which the component of the medical apparatus 100 is located (the current position).

Figure 4:
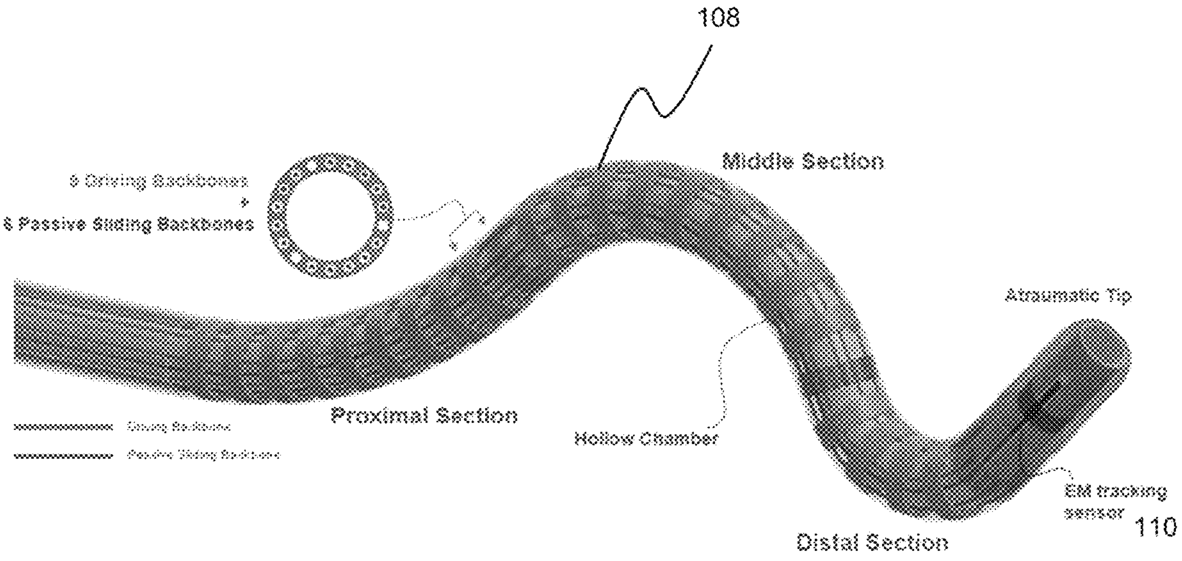
FIG. 4 is a catheter according to some embodiments.

The medical device 108 according to some embodiments can be configured as a catheter 108. As shown in FIG. 4, the catheter 108 includes a proximal section, a middle section, and a distal section. Each section can be bent by a plurality of driving wires (driving linear members) as driving backbones. The posture of the catheter 108 can be maintained by supporting wires (supporting linear members) as passive sliding backbones. The driving wires are connected to the actuator 106. The actuator 106 can include one or more motors and drives each section of the catheter 108 by pushing and/or pulling the driving wires.

The controller 102 can control the catheter 108 based on an algorithm known as follow-the-leader (FTL) algorithm. By applying the FTL algorithm, the middle section and the proximal section (following sections) of the catheter 108 move at a first position in the same way as the distal section moved at the first position or a second position near the first position.

In order to ensure catheter movement only occurs when the controller 102 is held and operated by the user intentionally, the hand-held controller 102 can include the movement-unlocking sensor 203 to distinguish an intended operation by a user from unintended operations.

The catheter movement is locked by the system until the movement-unlocking sensor 203 detects a user is holding the controller 102. When the movement-unlocking sensor 203 detects the user's holding, the controller 102 unlocks the catheter movement so that the user can control the catheter 108 with the controller 102.

Any combination of the following sensors and positions might be used as the movement-unlocking sensor 203.

The sensor 203 can be on the user interfacing surface of the hand-held controller which detects contact with a user's finger, thumb, or palm.

The sensor 203 can optically detect the user and can include a photodetector or the like.

The sensor 203 can be mechanical, e.g., slightly pressing down on a spring-loaded joystick can mechanically free the joystick to move.

The sensor 203 can be electrical where, for example, the user's skin can complete an electrical circuit, or slightly pressing down on the joystick can open or close an electrical circuitry to enable movement.

The sensor 203 can measure body temperature.

The sensor 203 can be placed on an underside of the controller 102 to detect a user's palm or fingers. The sensor 203 can be one or more or a combination of the above described optical/mechanical/electrical sensors.

An alternative method of achieving catheter movement control is to control catheter movement as a default, but lock movement if the robotic catheter 100 detects the controller 102 has been dropped.

One or more or a combination of the following sensors can detect a dropped state.

An accelerometer to detect acceleration or deceleration of a dropped controller due to gravity. If acceleration or deceleration is detected above a predetermined threshold, catheter movement can be locked.

A barometric pressure sensor to measure a relative vertical drop, e.g., the controller 102 is at a normal height of use, if it is dropped, the change in vertical position can trigger a movement lock.

As a reference, an Infineon Technology DPS310 barometric pressure sensor can measure relative vertical position to within +/−5 cm.

A further alternative method is to distinguish a user's holding from false activation of the movement-unlocking sensor. For example, the sensors can mistakenly interact to the environment when the controller 102 is put on a desk, or dropped on the floor.

At least two sensors can be mounted on two locations on the hand-held controller 102.

The medical apparatus according to some embodiments includes a medical device capable of maneuvering within a patient, an input device configured to be operated by a hand of a user, one or more sensors for sensing whether the hand of the user is interacting with the input device, and a controller configured to determine whether the one or more sensors is sensing that the hand of the user is interacting with the input device, and in a case that the controller determines that the one or more sensors is sensing that the hand of the user is not interacting with the input device, prevent actuation of the medical device.

The medical device can be a catheter. The input device can be one or more actuators configured to send one or more signals to the controller upon operation of the one or more actuators. The controller can actuate the medical device based on the one or more signals. The one or more actuators can include one or more levers and/or one or more buttons. The one or more sensors can be disposed on a surface of the one or more actuators. The one or more sensors can be an optical sensor, a mechanical sensor, or an electrical sensor.

In a case that the controller determines that the one or more sensors is sensing that the hand of the user is interacting with the input device, the controller can allow actuation of the medical device based on an input received by the input device. The one or more sensors can be further configured to sense whether the hand of the user is not interacting with the input device as a result of the input device being dropped. The one or more sensors can include an accelerometer configured to detect acceleration or deceleration of the input device. The one or more sensors can include a barometric pressure sensor configured to measure a relative vertical drop of the input device. The one or more sensors can include a first sensor located at a first location on the input device and a second sensor located at a second location on the input device. The first location corresponds to a palm of the hand of the user when the user is handling the input device and the second location corresponds to one or more fingers of the hand of the user when the user is handling the input device.

The controller can determine that the hand of the user is interacting with the input device when the first sensor detects the palm of the user interacting with the input device simultaneously with the second sensor detecting the one or more fingers of the user interacting with the input device. The controller can determine that the hand of the user is not interacting with the input device when either the first sensor does not detect the palm of the user interacting with the input device or the second sensor does not detect the one or more fingers of the user interacting with the input device. The input device can include a lever, and the second location is on the lever. The input device can include a protective structure configured to cover the second sensor while allowing the one or more fingers of the user to access the second sensor.

Figure 5:
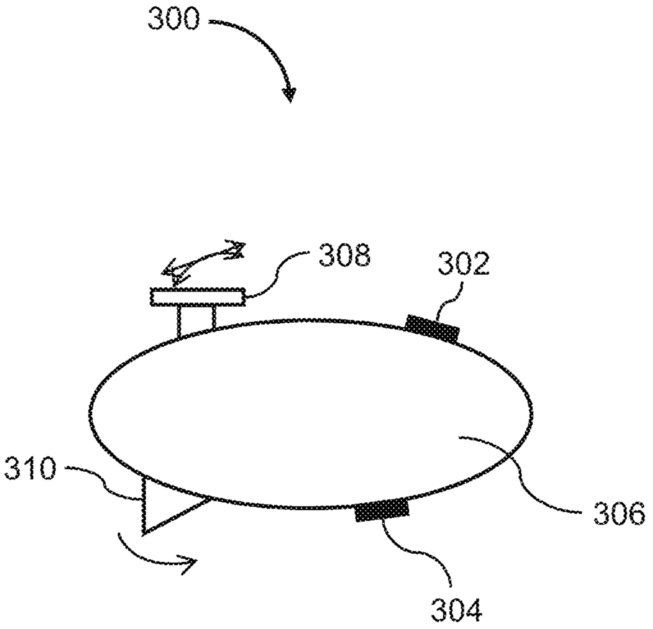
FIG. 5 is a controller according to some embodiments.

FIG. 5 illustrates a first embodiment of a controller 300 that includes a sensor in the form of a movement-unlocking sensor to distinguish an intended operation by a user from unintended operations to ensure catheter movement only occurs when the controller 300 is held and operated by the user intentionally. The controller 300 corresponds to the controller 102, and the robotic catheter 100 of FIGS. 1 and 2 can implement the first embodiment.

The hand-held controller 300 in FIG. 5 can have one or more of a palm optical sensor 302, a finger optical sensor 304, a grip 306, a lever 308, a trigger 310, and can include other elements or components. The palm optical sensor 302 and the finger optical sensor 304 are the movement unlock sensors. The palm optical sensor 302 and the finger optical sensor 304 are positioned on the grip 306 at different positions so that those sensors can be activated by the different positions of the user's palm and fingers. When the user holds the grip 306 to operate the lever 308 and the trigger 310, the palm optical sensor 302 and the finger optical sensor 304 can be activated by the palm and fingers respectively, and unlock the catheter movement. This unlock action will happen only with both activation of the palm optical sensor 302 and the finger optical sensor 304.

Therefore, when the hand-held controller 300 is dropped on the floor or put on the desk, the palm optical sensor 302 and finger optical sensor 304 cannot be activated simultaneously and can thereby avoid to unlock the catheter motion accidentally.

Figure 6:
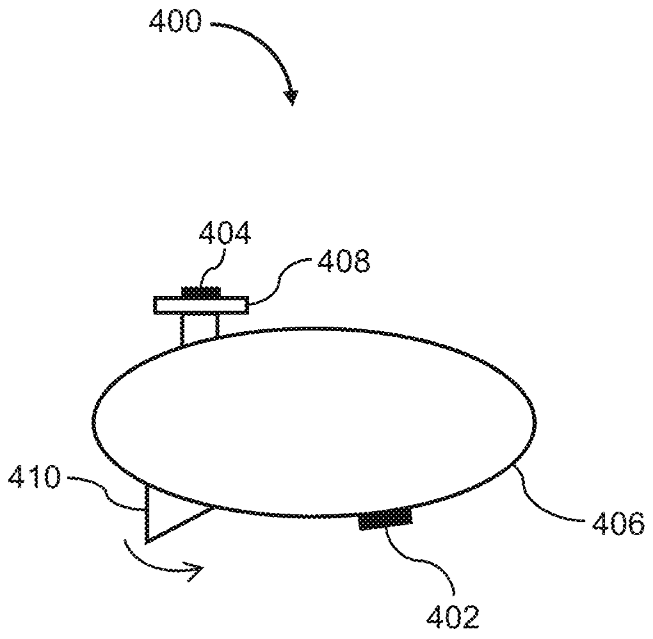
FIG. 6 is a controller according to some embodiments.

FIG. 6 illustrates a second embodiment of a controller 400 that includes a sensor in the form of a movement-unlocking sensor to distinguish an intended operation by a user from unintended operations to ensure catheter movement only occurs when the controller 400 is held and operated by the user intentionally. The controller 400 corresponds to the controller 102, and the robotic catheter 100 of FIGS. 1 and 2 can implement the second embodiment.

The hand-held controller 400 in FIG. 6 can have one or more of a palm optical sensor 402, a finger optical sensor 404, a grip 406, a lever 408, a trigger 410, and can include other elements or components. The palm optical sensor 402 and the finger optical sensor 404 are the movement unlock sensors. The palm optical sensor 302 is on the grip and the finger optical sensor 404 is on top of the lever 408. When the user holds the grip 406 to operate the lever 408 and the trigger 410, the palm optical sensor 402 and the finger optical sensor 404 can be activated by the palm and fingers respectively, and unlock the catheter movement. This unlock action will happen only with both activation of the palm optical sensor 402 and the finger optical sensor 404.

By positioning the palm optical sensor 402 on the grip 406 and the finger optical sensor 404 on the lever 408, when the hand-held controller 400 is dropped on the floor or put on the desk, the palm optical sensor 402 and finger optical sensor 404 cannot be activated simultaneously and can thereby avoid to unlock the catheter motion accidentally.

Figure 7:
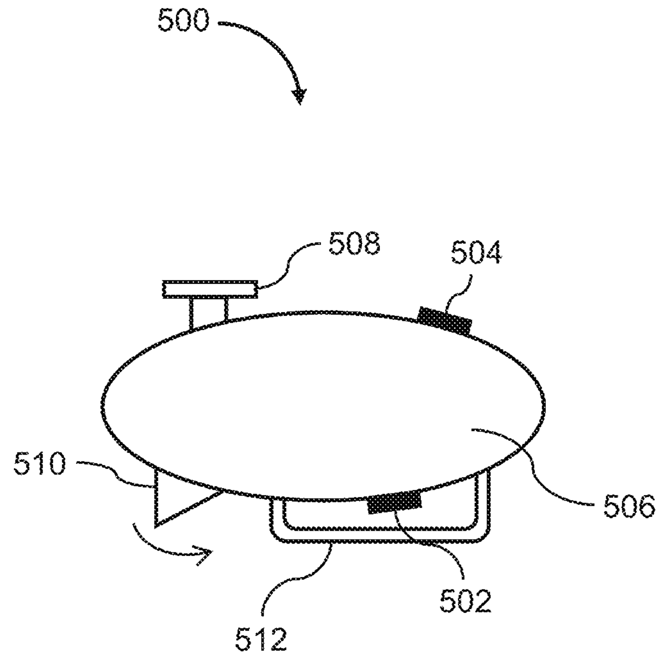
FIG. 7 is a controller according to some embodiments.
Figure 8:
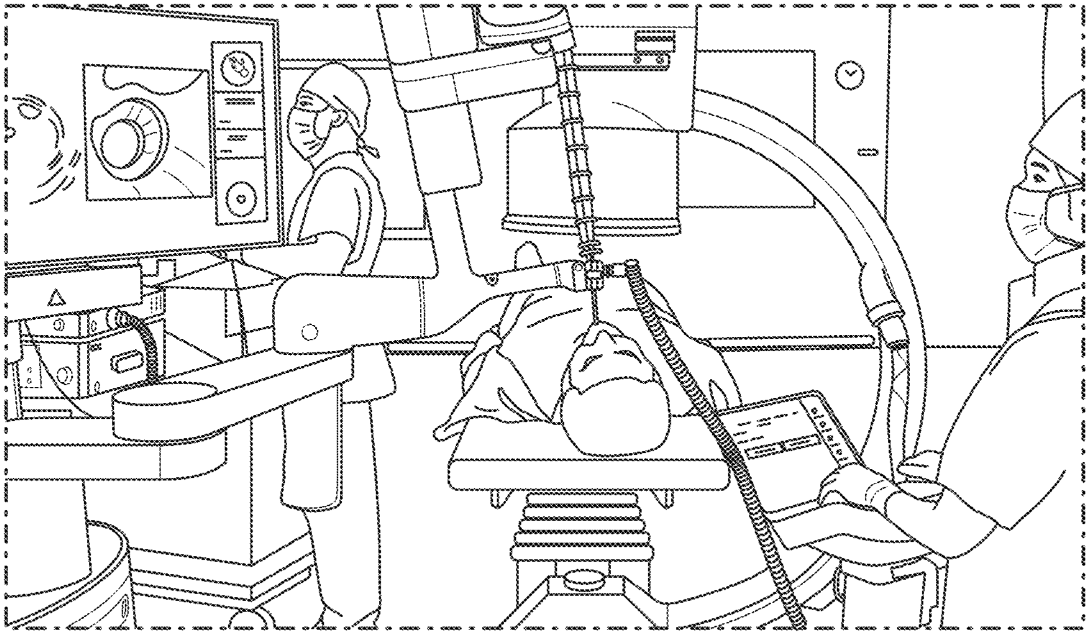
FIG. 8 (Prior Art)
FIG. 8 illustrates a prior art Intuitive Ion System.
Figure 9:
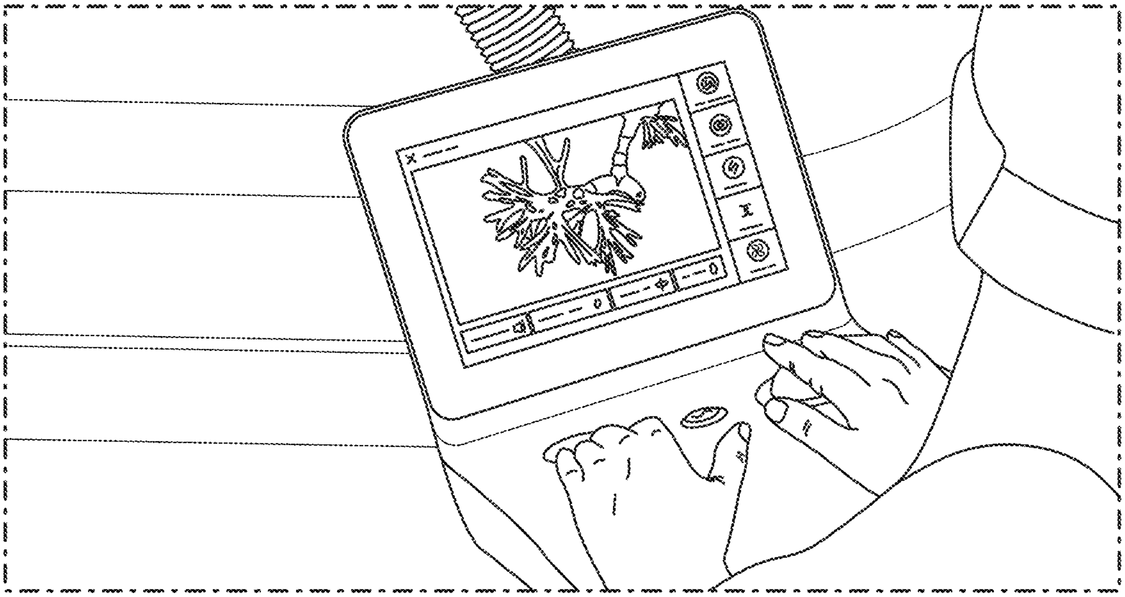
FIG. 9 (Prior Art)
FIG. 9 illustrates a prior art console of the Intuitive Ion System.
Figure 10:
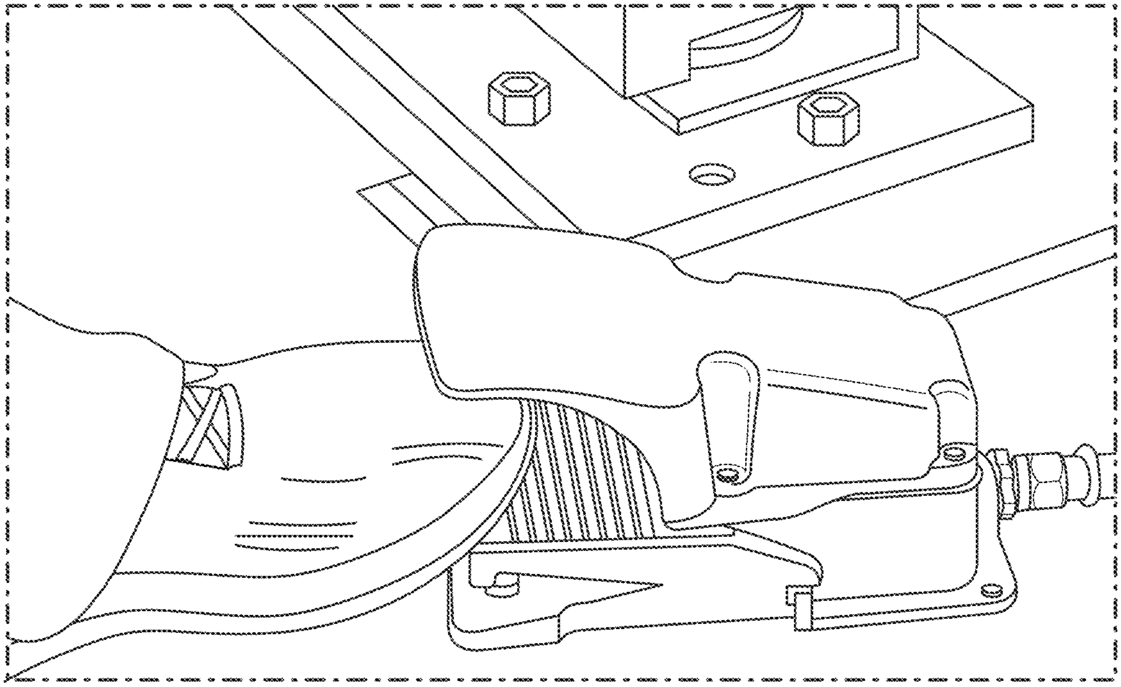
FIG. 10 (Prior Art)
FIG. 10 is a prior art safety foot pedal.
Figure 11:
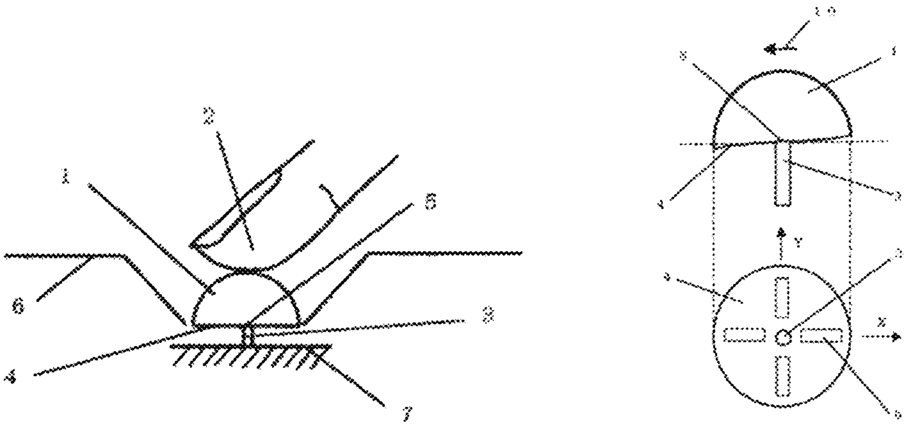
FIG. 11 PRIOR ART
FIG. 11 illustrates prior art figures of Japanese Publication No. 2004326713.

FIG. 7 illustrates a third embodiment of a controller 500 that includes a sensor in the form of a movement-unlocking sensor to distinguish an intended operation by a user from unintended operations to ensure catheter movement only occurs when the controller 500 is held and operated by the user intentionally. The controller 500/corresponds to the controller 102, and the robotic catheter 100 of FIGS. 1 and 2 can implement the third embodiment.

The hand-held controller 500 in FIG. 7 can have one or more of a palm optical sensor 502, a finger optical sensor 504, a grip 5o6, a lever 5o8, a trigger 510, and can include other elements or components. The controller 500 has an additional protective structure 512. The protective structure 512 for the movement-unlocking sensor makes environmental objects difficult to activate the movement-unlocking sensor.

The palm optical sensor 502 and the finger optical sensor 504 are the movement unlock sensors. The controller 500 includes two sensors 502, 504 on the grip at different positions so that those sensors can be activated by the different positions of the user's palm and fingers. When the user holds the grip 506 to operate the lever 508 and the trigger 510, the palm optical sensor 502 and the finger optical sensor 504 can be activated by the palm and fingers respectively, and unlock the catheter movement. This unlock action will happen only with both activation of the palm optical sensor 502 and the finger optical sensor 504.

The protective structure 512 covers the finger optical sensor 502 with enough gap to accept a user's fingers. Therefore, the user can still activate the finger optical sensor 502 with the fingers when the user holds the hand-held controller 500, but the surface of a floor or desk cannot activate the finger optical sensor 500.

Therefore, when the hand-held controller 500 is dropped on the floor or put on the desk, the palm optical sensor 502 and finger optical sensor 504 cannot be activated simultaneously and can thereby avoid to unlock the catheter motion accidentally.

There are several advantages over related art.

The Intuitive Ion System requires the relatively stationary surface (the cart) for the user to interface. The present disclosure is specifically designed for hand held controllers free to move in space.

The present disclosure overcomes the disadvantages of the foot pedal safety mechanism in that the foot pedal requires floor space. Correct movement stoppage is not ensured with the foot pedal because the controller could be dropped while the user is still activating the foot safety switch.

The sensor configuration in Japanese Publication No. 2004326713 is meant to toggle between joystick functions (i.e., pointing changed to scrolling and vice versa). The sensor configuration is not described as a safety mechanism to lock/unlock movement.

The apparatus of the present disclosure is a configuration described where the default state is not to allow movement of the medical device.

A sensor (or sensors) to detect the user is in contact with the controller, unlocking the system and allowing catheter movement.

The sensor can be one or more or a combination of optical, mechanical, or electrical by nature.

Alternately, the medical apparatus can have a default state of allowing movement.

Sensors can detect if the controller is dropped, thereby triggering a movement lock. The sensor (sensors) can be accelerometers to detect a drop. Or could be a sensor which measures relative height changes, like a barometric pressure sensor.

As described above, a medical apparatus according to some embodiments includes a medical device capable of maneuvering within a patient, an input device configured to be operated by a hand of a user, one or more sensors for sensing whether the hand of the user is interacting with the input device, and a controller configured to determine whether the one or more sensors is sensing that the hand of the user is interacting with the input device, and in a case that the controller determines that the one or more sensors is sensing that the hand of the user is not interacting with the input device, prevent actuation of the medical device.

The medical apparatus according to some embodiments includes a medical device capable of maneuvering within a patient, an input device configured to be operated by a hand of a user, one or more sensors for sensing whether the hand of a user is interacting with the input device, and a controller configured to determine whether the one or more sensors is sensing that the hand of the user is interacting with the input device, and in a case that the controller determines that the one or more sensors is sensing that the hand of the user is not interacting with the input device, prevent actuation of the medical device.

The medical device can be a catheter. The input device can be one or more actuators configured to send one or more signals to the controller upon operation of the one or more actuators. The controller can actuate the medical device based on the one or more signals. The one or more actuators can include one or more levers and/or one or more buttons. The one or more sensors can be disposed on a surface of the one or more actuators. The one or more sensors can be an optical sensor, a mechanical sensor, or an electrical sensor.

In a case that the controller determines that the one or more sensors is sensing that the hand of the user is interacting with the input device, the controller can allow actuation of the medical device based on an input received by the input device. The one or more sensors can be further configured to sense whether the hand of the user is not interacting with the input device as a result of the input device being dropped. The one or more sensors can include an accelerometer configured to detect acceleration or deceleration of the input device. The one or more sensors can include a barometric pressure sensor configured to measure a relative vertical drop of the input device. The one or more sensors can include a first sensor located at a first location on the input device and a second sensor located at a second location on the input device. The first location corresponds to a palm of the hand of the user when the user is handling the input device and the second location corresponds to one or more fingers of the hand of the user when the user is handling the input device.

The controller can determine that the hand of the user is interacting with the input device when the first sensor detects the palm of the user interacting with the input device simultaneously with the second sensor detecting the one or more fingers of the user interacting with the input device. The controller can determine that the hand of the user is not interacting with the input device when either the first sensor does not detect the palm of the user interacting with the input device or the second sensor does not detect the one or more fingers of the user interacting with the input device. The input device can include a lever, and the second location is on the lever. The input device can include a protective structure configured to cover the second sensor while allowing the one or more fingers of the user to access the second sensor.

At least some of the above-described apparatuses, methods, and mediums can be implemented, at least in part, by providing one or more computer-readable media that contain computer-executable instructions for realizing the above-described operations to one or more computing devices that are configured to read and execute the computer-executable instructions. The systems or devices perform the operations of the above-described embodiments when executing the computer-executable instructions. Also, an operating system on the one or more systems or devices may implement at least some of the operations of the above-described embodiments.

Furthermore, some embodiments use one or more functional units to implement the above-described apparatuses, methods, and mediums. The functional units may be implemented in only hardware (e.g., customized circuitry) or in a combination of software and hardware (e.g., a microprocessor that executes software).

Additionally, some embodiments of the apparatuses, methods, and mediums combine features from two or more of the embodiments that are described herein. Also, as used herein, the conjunction "or" generally refers to an inclusive "or," though "or" may refer to an exclusive "or" if expressly indicated or if the context indicates that the "or" must be an exclusive "or."

Various modifications and alterations based on the present disclosure may become apparent to those skilled in the art, and the features of the present disclosure may be applied to one or more configurational arrangements including, for example, CT, MRI, IVUS, PET, X-ray imaging, combinations or hybrids thereof, or the like.

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., central processing unit (CPU), micro processing unit (MPU), or the like), and may include a network of separate computers or separate processors to read out and execute the computer executable instructions. The computer executable instructions may be provided to the computerized configuration(s), for example, from a network or the storage medium. The storage medium may include, for example, one or more of a hard-disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A medical apparatus comprising:

a medical device capable of maneuvering within a patient;

an input device configured to be operated by a hand of a user;

one or more sensors for sensing whether the hand of the user is interacting with the input device, and whether the hand of the user is not interacting with the input device as a result of the input device being dropped; and a controller configured to:

determine whether the one or more sensors is sensing that the hand of the user is interacting with the input device;

prevent actuation of the medical device in a case that the controller determines that the one or more sensors is sensing that the hand of the user is not interacting with the input device; and allow actuation of the medical device in a case that the controller determines that the one or more sensors is sensing that the hand of the user is interacting with the input device, wherein one or more sensors comprises a first sensor located at a first location on the input device and a second sensor located at a second location on the input device, and wherein the first location corresponds to a palm of the hand of the user when the user is handling the input device and the second location corresponds to one or more fingers of the hand of the user when the user is handling the input device.

2. The medical apparatus of claim 1, wherein the medical device is a catheter.

3. The medical apparatus of claim 1, wherein the input device comprises one or more actuators configured to send one or more signals to the controller upon operation of the one or more actuators; and wherein the controller is further configured to actuate the medical device based on the one or more signals.

4. The medical apparatus of claim 3, wherein the one or more actuators comprises one or more levers and/or one or more buttons.

5. The medical apparatus of claim 3, wherein the one or more sensors is disposed on a surface of the one or more actuators.

6. The medical apparatus of claim 1, wherein the one or more sensors is an optical sensor.

7. The medical apparatus of claim 1, wherein the one or more sensors is a mechanical sensor.

8. The medical apparatus of claim 1, wherein the one or more sensors is an electrical sensor.

9. The medical apparatus of claim 1, wherein, in a case that the controller determines that the one or more sensors is sensing that the hand of the user is interacting with the input device, the controller is further configured to allow actuation of the medical device based on an input received by the input device.

10. The medical apparatus of claim 1, wherein the one or more sensors comprises an accelerometer configured to detect acceleration or deceleration of the input device.

11. The medical apparatus of claim 1, wherein the one or more sensors comprises a barometric pressure sensor configured to measure a relative vertical drop of the input device.

12. The medical apparatus of claim 1, wherein the controller determines that the hand of the user is interacting with the input device when the first sensor detects the palm of the user interacting with the input device simultaneously with the second sensor detecting the one or more fingers of the user interacting with the input device.

13. The medical apparatus of claim 1, wherein the controller determines that the hand of the user is not interacting with the input device when either the first sensor does not detect the palm of the user interacting with the input device or the second sensor does not detect the one or more fingers of the user interacting with the input device.

14. The medical apparatus of claim 1, wherein the input device comprises a lever; and wherein the second location is on the lever.

15. The medical apparatus of claim 1, wherein the input device comprises a protective structure configured to cover the second sensor while allowing the one or more fingers of the user to access the second sensor.

16. A method for a medical apparatus, the method comprising:

maneuvering a medical device within a patient;

operating an input device by a hand of a user;

sensing, using one or more sensors, whether the hand of the user is interacting with the input device, and whether the hand of the user is not interacting with the input device as a result of the input device being dropped;

determining whether the one or more sensors is sensing that the hand of the user is interacting with the input device;

preventing actuation of the medical device in a case that the determining determines that the one or more sensors is sensing that the hand of the user is not interacting with the input device, preventing actuation of the medical device; and allowing actuation of the medical device in a case that the determining determines that the one or more sensors is sensing that the hand of the user is interacting with the input device, wherein one or more sensors comprises a first sensor located at a first location on the input device and a second sensor located at a second location on the input device, and wherein the first location corresponds to a palm of the hand of the user when the user is handling the input device and the second location corresponds to one or more fingers of the hand of the user when the user is handling the input device.

17. A storage medium storing a program for causing a computer to execute a method for a medical apparatus, the method comprising:

maneuvering a medical device within a patient;

operating an input device by a hand of a user;

sensing, using one or more sensors, whether the hand of the user is interacting with the input device, and whether the hand of the user is not interacting with the input device as a result of the input device being dropped;

determining whether the one or more sensors is sensing that the hand of the user is interacting with the input device;

preventing actuation of the medical device in a case that the determining determines that the one or more sensors is sensing that the hand of the user is not interacting with the input device; and allowing actuation of the medical device in a case that the determining determines that the one or more sensors is sensing that the hand of the user is interacting with the input device, wherein one or more sensors comprises a first sensor located at a first location on the input device and a second sensor located at a second location on the input device, and wherein the first location corresponds to a palm of the hand of the user when the user is handling the input device and the second location corresponds to one or more fingers of the hand of the user when the user is handling the input device.

* * * * *